United States Patent
Song et al.

(10) Patent No.: US 11,491,071 B2
(45) Date of Patent: Nov. 8, 2022

(54) VIRTUAL SCENE INTERACTIVE REHABILITATION TRAINING ROBOT BASED ON LOWER LIMB CONNECTING ROD MODEL AND FORCE SENSE INFORMATION AND CONTROL METHOD THEREOF

(71) Applicant: SOUTHEAST UNIVERSITY, Jiangsu (CN)

(72) Inventors: Aiguo Song, Jiangsu (CN); Ke Shi, Jiangsu (CN); Hong Zeng, Jiangsu (CN); Huijun Li, Jiangsu (CN); Baoguo Xu, Jiangsu (CN); Xinyu Tang, Jiangsu (CN)

(73) Assignee: SOUTHEAST UNIVERSITY, Jiangsu (CN)

( * ) Notice: Subject to any disclaimer, the term of this patent is extended or adjusted under 35 U.S.C. 154(b) by 293 days.

(21) Appl. No.: 16/907,182

(22) Filed: Jun. 20, 2020

(65) Prior Publication Data
US 2020/0315895 A1    Oct. 8, 2020

Related U.S. Application Data

(63) Continuation-in-part of application No. PCT/CN2018/088079, filed on May 23, 2018.

(30) Foreign Application Priority Data

Dec. 21, 2017 (CN) .......................... 201711394155.8

(51) Int. Cl.
*A61H 1/02* (2006.01)
*A61B 5/103* (2006.01)
(Continued)

(52) U.S. Cl.
CPC ......... *A61H 1/0262* (2013.01); *A61B 5/1038* (2013.01); *A61B 5/112* (2013.01);
(Continued)

(58) Field of Classification Search
CPC ................ A61H 1/0262; A61H 1/0229; A61H 2201/1642; A61H 2201/5061;
(Continued)

(56) References Cited

U.S. PATENT DOCUMENTS 4,620,703 A * 11/1986 Greenhut ............. A63B 21/153
 482/901
4,635,875 A * 1/1987 Apple .................... B66D 1/741
 254/294

(Continued)

*Primary Examiner* — Garrett K Atkinson
(74) *Attorney, Agent, or Firm* — JCIPRNET (57) ABSTRACT

A virtual scene interactive rehabilitation training robot based on a lower limb connecting rod model and force sense information and a control method thereof are disclosed. The thigh, calf and foot of a leg of a human body are equated to a three-connecting rod series-connected mechanical arm. A human body leg gravity compensation model is constructed. The leg posture of a patient is detected by Kinect. An interaction force between a limb of the patient and a rehabilitation robot is detected by a force sensor on the rehabilitation robot. Then, a progressive rehabilitation training method is designed for the model. According to a set weight reduction ratio, the motion of the rehabilitation robot is controlled by judging plantar force data.

4 Claims, 5 Drawing Sheets

(51) Int. Cl.
*A61B 5/11* (2006.01)
*A63B 21/00* (2006.01)
*A63B 71/06* (2006.01)
*G06F 3/01* (2006.01)

(52) U.S. Cl.
CPC ..... *A61H 1/0229* (2013.01); *A63B 21/00181* (2013.01); *A63B 71/0622* (2013.01); *G06F 3/011* (2013.01); *A61H 2201/1642* (2013.01); *A61H 2201/5061* (2013.01); *A61H 2205/10* (2013.01); *A61H 2230/625* (2013.01); *A63B 2071/0638* (2013.01); *G06F 2203/012* (2013.01)

(58) Field of Classification Search
CPC .......... A61H 2205/10; A61H 2230/625; A61H 1/00; A61H 1/0237; A61H 1/0218; A61B 5/1038; A61B 5/112; A63B 21/00181; A63B 71/0622; A63B 2071/0638; G06F 3/011; G06F 2203/012
See application file for complete search history.

(56) References Cited

U.S. PATENT DOCUMENTS

| | | | | |
|---|---|---|---|---|
| 4,724,827 | A * | 2/1988 | Schenck | A61H 1/0288 601/40 |
| 5,667,461 | A * | 9/1997 | Hall | A63B 69/0064 482/54 |
| 6,123,649 | A * | 9/2000 | Lee | A63B 21/4013 482/54 |
| 6,146,315 | A * | 11/2000 | Schonenberger | A63B 22/02 482/54 |
| 6,666,831 | B1 * | 12/2003 | Edgerton | A63B 69/0064 600/595 |
| 6,689,075 | B2 * | 2/2004 | West | A61H 1/0262 482/69 |
| 6,796,926 | B2 * | 9/2004 | Reinkensmeyer | A61H 3/008 482/8 |
| 6,821,233 | B1 * | 11/2004 | Colombo | A61H 1/0262 601/5 |
| 7,331,906 | B2 * | 2/2008 | He | A61H 1/0237 482/69 |
| 7,494,450 | B2 * | 2/2009 | Solomon | A63B 21/00181 482/69 |
| 7,887,471 | B2 * | 2/2011 | McSorley | A63B 21/0552 482/136 |
| 7,998,040 | B2 * | 8/2011 | Kram | A63B 21/055 482/54 |
| 8,057,410 | B2 * | 11/2011 | Angold | A61H 3/00 601/5 |
| 8,608,479 | B2 * | 12/2013 | Liu | A61H 3/04 434/255 |
| 8,920,347 | B2 * | 12/2014 | Bayerlein | A63B 21/00181 601/5 |
| 9,638,163 | B2 * | 5/2017 | Holloway | B66C 13/08 |
| 9,789,023 | B1 * | 10/2017 | Lee | A63B 24/0062 |
| 9,981,157 | B2 * | 5/2018 | Bayerlein | A63B 21/00178 |
| 10,278,883 | B2 * | 5/2019 | Walsh | G16H 20/30 |
| 10,342,461 | B2 * | 7/2019 | Basta | A61B 5/1038 |
| 10,465,663 | B2 * | 11/2019 | Holloway | B66C 13/08 |
| 10,548,800 | B1 * | 2/2020 | Barnes | A61H 1/0244 |
| 10,596,057 | B2 * | 3/2020 | Branch | A61B 5/1122 |
| 10,925,796 | B2 * | 2/2021 | Fukunaga | A61H 1/024 |
| 2003/0064869 | A1 * | 4/2003 | Reinkensmeyer | A61H 3/008 482/8 |
| 2004/0097330 | A1 * | 5/2004 | Edgerton | A61H 1/0262 482/54 |
| 2005/0101448 | A1 * | 5/2005 | He | A61H 1/0255 482/69 |
| 2008/0255488 | A1 * | 10/2008 | Agrawal | A63B 69/0064 623/24 |
| 2008/0300118 | A1 * | 12/2008 | Wehrell | A63B 21/169 482/129 |
| 2010/0285929 | A1 * | 11/2010 | Bayerlein | A61H 1/024 482/54 |
| 2012/0004581 | A1 * | 1/2012 | Dinon | A61H 1/0237 601/23 |
| 2013/0225371 | A1 * | 8/2013 | Harrer | A63B 21/4017 482/8 |
| 2014/0121071 | A1 * | 5/2014 | Strom | A63B 21/062 482/99 |
| 2015/0232307 | A1 * | 8/2015 | Holloway | B66C 13/08 254/338 |
| 2017/0218927 | A1 * | 8/2017 | Holloway | F03D 80/50 |
| 2018/0071162 | A1 * | 3/2018 | Branch | A61H 1/008 |
| 2021/0369533 | A1 * | 12/2021 | Huang | A61H 3/00 |

* cited by examiner

VIRTUAL SCENE INTERACTIVE REHABILITATION TRAINING ROBOT BASED ON LOWER LIMB CONNECTING ROD MODEL AND FORCE SENSE INFORMATION AND CONTROL METHOD THEREOF

CROSS-REFERENCE TO RELATED APPLICATION

This application is a continuation in part of international PCT application serial no. PCT/CN2018/088079, filed on May 23, 2018, which claims the priority benefit of China application no. 201711394155.8, filed on Dec. 21, 2017. The entirety of each of the above-mentioned patent applications is hereby incorporated by reference herein and made a part of this specification.

BACKGROUND

Technical Field

The present invention belongs to a robot control technology, and more particularly, to a virtual scene interactive rehabilitation training robot based on a lower limb connecting rod model and force sense information and a control method thereof.

Description of Related Art

A robot technology is developing rapidly at present. A rehabilitation training robot is an important branch thereof. How to make a patient and the robot react more friendly in the process of rehabilitation training using the rehabilitation training robot to achieve comfortable, efficient and well-adapted rehabilitation training is a problem to be solved.

In the rehabilitation training process, existing rehabilitation training robots generally perform weight compensation on the limbs of the patient through mechanical structures, which is likely to make the patient feel uncomfortable. For multi-freedom robots, a mechanical structure weight compensation scheme is not suitable, and a torque estimation method is usually used. However, this method has a large error. In addition, the traditional rehabilitation training process is relatively simple, and only a monotonous repetitive motion is used to achieve rehabilitation during a rehabilitation training cycle. Therefore, it is of great value to develop a comfortable and efficient rehabilitation training method based on a rehabilitation training robot.

SUMMARY

Purpose of the invention: The purpose of the present invention is to solve the defects in the existing technology, and to provide a virtual scene interactive rehabilitation training robot based on a lower limb connecting rod model and force sense information and a control method thereof, which are used for the rehabilitation training robot to assist in rehabilitation training.

Technical solution is described below. A virtual scene interactive rehabilitation training robot based on a lower limb linkage model and force sense information described in the present invention includes a thigh mechanical arm, a calf mechanical arm and a foot mechanical arm that are movably connected in sequence from top to bottom. A six-dimensional force sensor is installed on the foot mechanical arm. A thigh, a calf and a foot of a patient are fixed to the corresponding thigh mechanical arm, calf mechanical arm and foot mechanical arm in sequence. The thigh, the calf and the foot of a leg of the patient are equated to a three-connecting rod series-connected mechanical arm.

The present invention also discloses a control method of a virtual scene interactive rehabilitation training robot based on a lower limb linkage model and force sense information. The method includes following steps. Equating the thigh, the calf and the foot of a leg of the patient to a three-connecting rod series-connected mechanical arm. Constructing a human body leg gravity compensation model. Detecting the leg posture of the patient by Kinect. Detecting an interaction force between a limb of the patient and a rehabilitation robot by a six-dimensional force sensor. When the leg of the patient is relaxed, namely, in a state of no active force, driving, by the rehabilitation training robot, the limb of the patient to move slowly at a constant speed for several cycles along a preset trajectory in a controller, correcting the human body leg gravity compensation model after acquiring posture information of the patient and corresponding force information, adopting a progressive rehabilitation training method for the human body leg gravity compensation model after correcting the model, and controlling, according to a set weight reduction ratio, the motion of the rehabilitation robot by judging data of a plantar six-dimensional force sensor.

The human body leg gravity compensation model is as follows.

(1) A leg of a human body is equated to a mechanical arm having three series-connected connecting rods, the foot, the calf and the thigh are a connecting rod T0S0, a connecting rod S0F0 and a connecting rod F0S0, respectively, the foot and the sensor are relatively stationary, and parts other than the leg of the human body are equated to a base (Base) in a stationary state.

(2) A hip joint coordinate system, a knee joint coordinate system and an ankle joint coordinate system are established, the six-dimensional force sensor on the robot and the foot of the human body of the patient are relatively stationary, then a coordinate system is established by taking a contact point between the six-dimensional force sensor and the foot of the patient as an S0 origin, an X axis, a Y axis and a Z axis of the coordinate system are parallel to an X axis, a Y axis and a Z axis of the ankle joint coordinate system, respectively, and positive directions of the three axes are the same as a positive direction of the ankle joint coordinate system.

In a center of a mass coordinate system corresponding to the thigh, the calf and the foot of the patient, centers of mass ET0, EC0 and EF0 of corresponding parts of the leg are taken as an origin, a vertical downward direction is a Z axis positive direction, an outward direction perpendicular to a human body plane is an X axis positive direction, and a direction perpendicular to an XZ plane toward the human body is a Y axis positive direction.

(3) It is assumed that $^{ET}F_{mg}$, $^{EC}F_{mg}$, and $^{EF}F_{mg}$ are gravity vectors of the thigh, calf and foot in a geodetic coordinate system, $^{A}_{B}R$ is a rotation matrix from a B coordinate system to an A coordinate system, $^{A}_{B}T_f$ is a force parameter conversion matrix from the B coordinate system to the A coordinate system, and $^{A}P_{BORG}$ is a representation of an origin of the B coordinate system in the A coordinate system. An equation is obtained:

$$^{A}_{B}T_f = \begin{bmatrix} ^{A}_{B}R & 0 \\ ^{A}P_{BORG} \times ^{A}_{B}R & ^{A}_{B}R \end{bmatrix}$$

An interference force caused by a thigh gravity and its joint damping with a trunk and due to individual errors (such as a center of mass position and a leg mass) of average characteristic parameters is represented as $^{ST}F_{mg}$ in a six-dimensional force sensor coordinate system; an interference force caused by a calf gravity and its joint damping with the thigh and due to the individual errors of the average characteristic parameters is represented as $^{SC}F_{mg}$ in the sensor coordinate system; an interference force caused by a foot gravity and its joint damping with the calf and due to the individual errors of the average characteristic parameters is represented as $^{SF}F_{mg}$ in the sensor coordinate system; $_{ET}^S E$, $_{EC}^S E$ and $_{EF}^S E$ are interference correction parameter matrices caused due to the individual errors of the average characteristic parameters of the thigh, the calf and the foot, respectively; $_{ET}^S T_f$, $_{EC}^S T_f$ and $_{EF}^S T_f$ are parameter conversion matrices of the thigh, the calf and the foot from the geodetic coordinate system to the force sensor coordinate system, respectively; $C_f$ is an interference correction parameter matrix caused due to joint damping, left superscripts B, T and C representing the hip, knee, and ankle joints, respectively; $^S F_{mg}$ is a plantar force acting on a force sensor;

Following equations are derived:

$$^{ST}F_{mg} = {}_{ET}^S E \times {}_{ET}^S T_f \times {}^{ET}F_{mg} + {}_{ET}^S T_f \times {}_T^{ET} R \times {}_B^T R \times {}^B C_f$$

$$^{SC}F_{mg} = {}_{EC}^S E \times {}_{EC}^S T_f \times {}^{EC}F_{mg} + {}_{EC}^S T_f \times {}_C^{EC} R \times {}_T^C R \times {}^T C_f$$

$$^{SF}F_{mg} = {}_{EF}^S E \times {}_{EF}^S T_f \times {}^{EF}F_{mg} + {}_{EF}^S T_f \times {}_F^{EF} R \times {}_C^F R \times {}^C C_f$$

$$^S F_{mg} = {}^{ST}F_{mg} + {}^{SC}F_{mg} + {}^{SF}F_{mg}$$

(3) The human body leg gravity compensation model is obtained by steps (1) to (2), an initial model is established by inputting height and weight parameters of the patient into the controller, plantar six-dimensional force sensor parameters in the absence of an active force in any posture of a user are acquired by the model, actual parameters and the parameters acquired by the model are input into the controller, and the rehabilitation robot is controlled to interact with the patient using a progressive rehabilitation training control method.

The method of establishing the three coordinate systems in step (2) is described below.

The hip joint coordinate system: a human body stands with legs closed, a center point T0 at a connection between the thigh and the trunk is taken as an origin of the hip joint coordinate system, an axial downward direction along the thigh is a TX axis positive direction, an outward direction perpendicular to a front surface of the human body is a TZ axis positive direction, and a direction perpendicular to a TXTZ plane toward the trunk of the human body is a TY axis positive direction.

The knee joint coordinate system: a human body stands with legs closed, a center point C0 at a connection between the thigh and the calf is taken as an origin of the knee joint coordinate system, an axial downward direction along the knee is a CX axis positive direction, an outward direction perpendicular to a front surface of the human body is a CZ axis positive direction, and a direction perpendicular to a CXCZ plane toward the trunk of the human body is a CY axis positive direction.

The ankle joint coordinate system: a human body stands with legs closed, a center point F0 at a connection between the thigh, the calf and the foot is taken as an origin of the ankle joint coordinate system, an axial outward direction along the foot is an FX axis positive direction, a direction perpendicular to an F0FX plane and an F0C0 plane toward the trunk of the human body is an FY axis positive direction, and a direction perpendicular to an FXFY plane toward the trunk of the human body is an FZ axis positive direction.

In a coordinate system established by taking a contact point between the six-dimensional force sensor and the foot of the patient as an S0 origin, an SX axis is parallel to an FX axis, an SY axis is parallel to an FY axis, and an SZ axis is parallel to an FZ axis.

The specific process of the progressive rehabilitation training control method is as follows.

(A) First, importing the human body leg gravity compensation model into the controller, running along a preset trajectory for several cycles in a working space, and correcting $_E^S E$ and $C_f$ in the model by an acquired six-dimensional force sensor value and a corresponding posture to obtain a characteristic model for the patient finally.

(B) Detecting the leg posture of a user using Kinect, detecting a plantar force of the user using the six-dimensional force sensor, and controlling the robot to interact with the patient according to a virtual reality scene in step (C).

(C) In combination with a gentle slope virtual scene, according to a gradient of a gentle slope where a virtual character is located currently, determining an active force required by the patient at this moment through the human body leg gravity compensation model, and controlling the robot to move according to regulations of step (D) through the acquired force and posture situations in step (D).

(D) Obtaining a gravity value of a current posture according to the human body leg gravity compensation model, obtaining a value of an active force required currently according to a virtual reality model, comparing the sizes of values obtained by the force sensor currently, if a value obtained by the six-dimensional force sensor currently is greater than the sum of the gravity value and the active force required, allowing the robot to move, or otherwise keeping the robot stationary.

In a rehabilitation cycle, the gradient of a virtual scene is gradually increased, that is, the value of a required active force is increased, and the physical function of the patient is progressively restored until the limb motion may be freely controlled.

Beneficial Effects: compared with the existing technology, the present invention has the following advantages.

(1) The rehabilitation training weight compensation model in the present invention may be applied to any rehabilitation training robot with a force sensor, regardless of an exoskeleton rehabilitation training robot or an end rehabilitation training robot.

(2) In the present invention, there is no need to wear an additional posture sensor, and only a Kinect camera used as a virtual reality interactive input device in a rehabilitation training system is adopted.

(3) The present invention is good in applicability and can be adapted to patients with different weights and heights, compensation models corresponding to patients with different body types can be obtained through the correction of compensation parameters in a human body leg gravity compensation model, and calculation errors of a weight compensation model can also be reduced.

(4) In the present invention, in combination with a virtual scene and a progressive rehabilitation training method, the patients can be rehabilitated unconsciously. On the one hand, the progressive rehabilitation training method can make the patients gradually improve the difficulty of rehabilitation training. On the other hand, the intervention of the virtual scene can make the patients have a clear perception of their physical function.

DESCRIPTION OF THE EMBODIMENTS

The technical solutions of the present invention are described in detail below, but the protection scope of the present invention is not limited to the embodiments.

As shown in FIG. 1 to FIG. 4, a virtual scene interactive rehabilitation training robot based on a lower limb connecting rod model and force sense information of the present invention is mainly a rehabilitation training gravity compensation model based on force sense information and a progressive rehabilitation training method based on the model and virtual reality. First, a leg (thigh, calf and foot) of a human body is equated to a three-connecting rod series-connected mechanical arm, a human body leg gravity compensation model is constructed, a leg posture of a patient is detected by Kinect, an interaction force between a limb of the patient and a rehabilitation robot is detected by a force sensor on the rehabilitation robot. When the leg of a user is relaxed, namely, in a state of no active force, the rehabilitation training robot drives the limb of the patient to move slowly at a constant speed for multiple cycles along a preset trajectory, and the compensation model is corrected after posture information and corresponding force information are acquired. The progressive rehabilitation training method is designed for the model after the model is corrected, and the motion of the rehabilitation robot is controlled by judging data of a plantar force sensor 5 according to a set weight reduction ratio.

Figure 1:
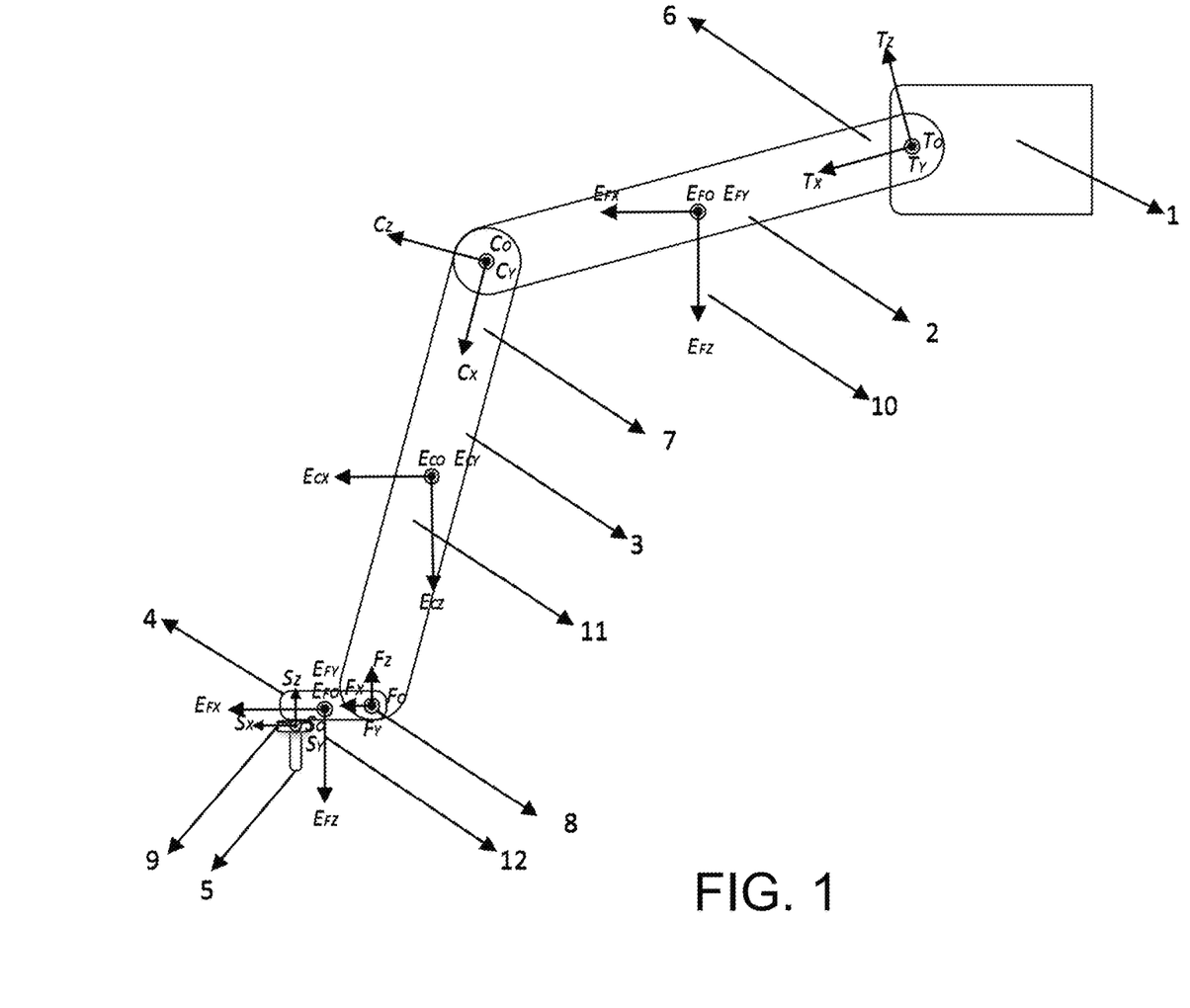
FIG. 1 is a schematic construction diagram of an overall model in the present invention.

The leg gravity compensation model is as follows.

a) A leg of a human body is equated to a mechanical arm having three series-connected connecting rods, a foot 4, a calf 3 and a thigh 2 are a connecting rod T0S0, a connecting rod S0F0 and a connecting rod F0S0, respectively, the foot and the sensor are relatively stationary, and parts other than the leg of the human body are equated to a base (Base1) in a stationary state.

b) Each joint coordinate system is established, the human body stands with legs closed, a center point T0 at a connection between the thigh 2 and the trunk is taken as an origin of a hip joint coordinate system 6, an axial downward direction along the thigh 2 is a TX axis positive direction, an outward direction perpendicular to a front surface of the human body is a TZ axis positive direction, and a direction perpendicular to a TXTZ plane toward the trunk of the human body is a TY axis positive direction. Similarly, a knee joint coordinate system 7 and an ankle joint coordinate system 8 are established. The six-dimensional force sensor 5 and the foot 4 of the human body are relatively stationary. Then, a contact point between the sensor and the foot 4 is taken as an S0 origin, an SX axis is parallel to an FX axis, an SY axis is parallel to an FY axis, an SZ axis is parallel to an FZ axis, and positive directions of the three axes are the same as a positive direction of the ankle joint coordinate system 8. In a center of mass coordinate system corresponding to each part of the leg (the thigh 2, the calf 3 and the foot 4), the centers of mass (ETO, ECO and EFO) of each part of the leg are taken as an origin, a vertical downward direction is a Z axis positive direction, an outward direction perpendicular to a human body plane is an X axis positive direction, and a direction perpendicular to an XZ plane toward the human body is a Y axis positive direction.

c) It is assumed that $^{ET}F_{mg}$, $^{EC}F_{mg}$, and $^{EF}F_{mg}$ are gravity vectors of the thigh 2, the calf 3 and the foot 4 in a geodetic coordinate system, $_B^A R$ is a rotation matrix from a B coordinate system to an A coordinate system, $_B^A T_f$ is a force parameter conversion matrix from the B coordinate system to the A coordinate system, and $^A P_{BORG}$ is a representation of an origin of the B coordinate system in the A coordinate system. An equation is obtained:

$$_B^A T_f = \begin{bmatrix} _B^A R & 0 \\ ^A P_{BORG} \times _B^A R & _B^A R \end{bmatrix}$$

An interference force caused by the gravity of the thigh 2 and its joint damping with the trunk and due to individual errors (such as a center of mass position and a leg mass) of average characteristic parameters is represented as $^{ST}F_{mg}$ in a sensor coordinate system, an interference force caused by the gravity of the calf 3 and its joint damping with the thigh 2 and due to the individual errors of the average characteristic parameters is represented as $^{ST}F_{mg}$ in the sensor coordinate system, and an interference force caused by the gravity of the foot 4 and its joint damping with the calf 3 and due to the individual errors of the average characteristic parameters is represented as $^{ST}F_{mg}$ in the sensor coordinate system. $_E^S E$ is an interference correction parameter matrix caused due to the individual errors of the average characteristic parameters, and $C_f$ is an interference correction parameter matrix caused due to joint damping.

The following equations are derived.

$$^{ST}F_{mg} = _{ET}^S E \times _{ET}^S T_f \times ^{ET}F_{mg} + _{ET}^S T_f \times _T^{ET}R \times _B^T R \times ^B C_f$$

$$^{SC}F_{mg} = _{EC}^S E \times _{EC}^S T_f \times ^{EC}F_{mg} + _{EC}^S T_f \times _C^{EC}R \times _T^C R \times ^T C_f$$

$$^{SF}F_{mg} = _{EF}^S E \times _{EF}^S T_f \times ^{EF}F_{mg} + _{EF}^S T_f \times _F^{EF}R \times _C^F R \times ^C C_f$$

$$^S F_{mg} = ^{ST}F_{mg} + ^{SC}F_{mg} + ^{SF}F_{mg}$$

d) The human body leg gravity compensation model is obtained by steps a) to c), an initial model is established by inputting height and weight parameters of the user, and parameters of the plantar six-dimensional force sensor 5 in the absence of an active force in any posture of the user are acquired by the model. Actual parameters and the parameters acquired by the model are input into the controller, and the rehabilitation robot is controlled to interact with the user according to the progressive rehabilitation training control method.

Figure 2:
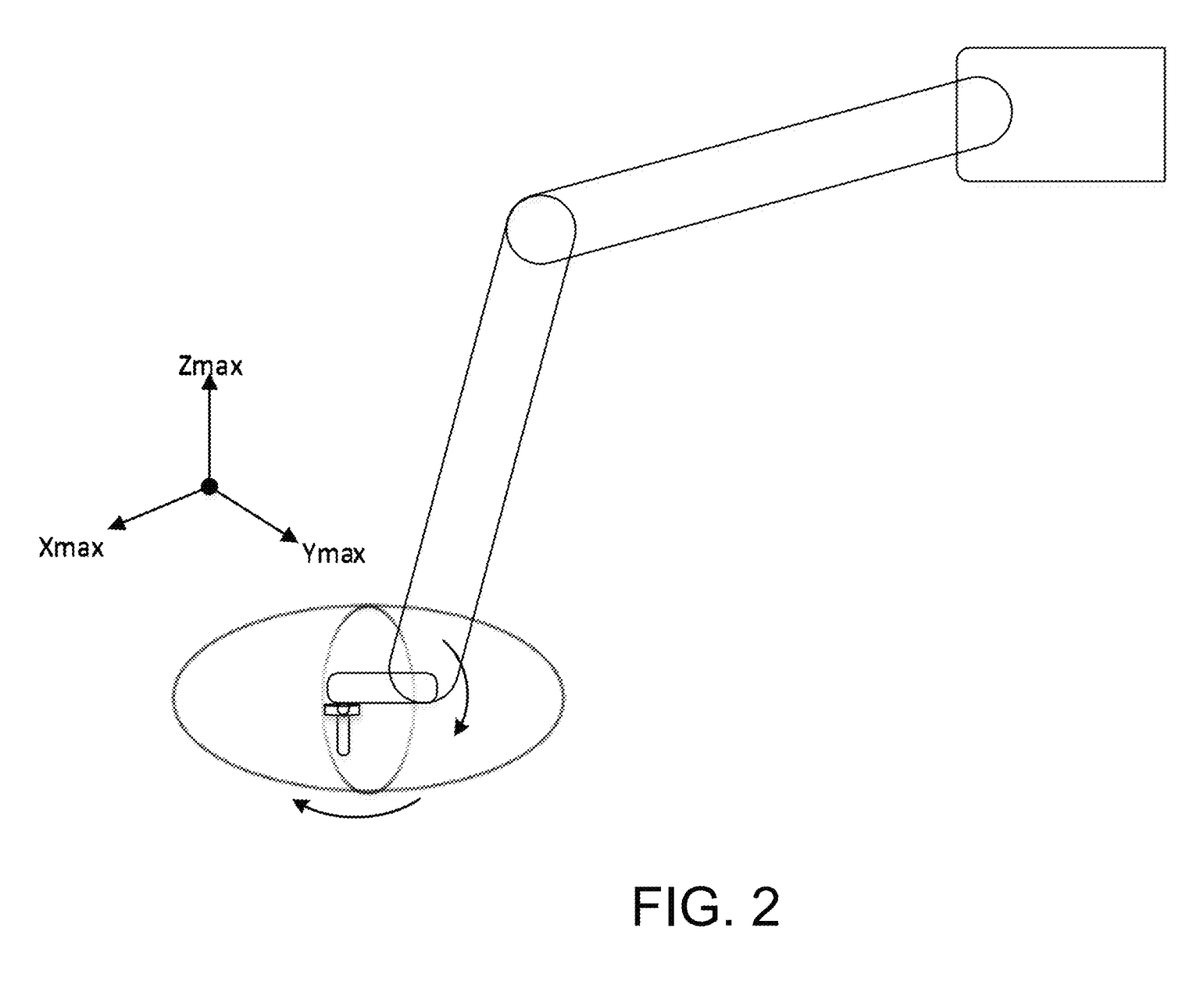
FIG. 2 is a schematic setting diagram of a human body leg gravity compensation model correcting a motion trajectory in the present invention.
Figure 3:
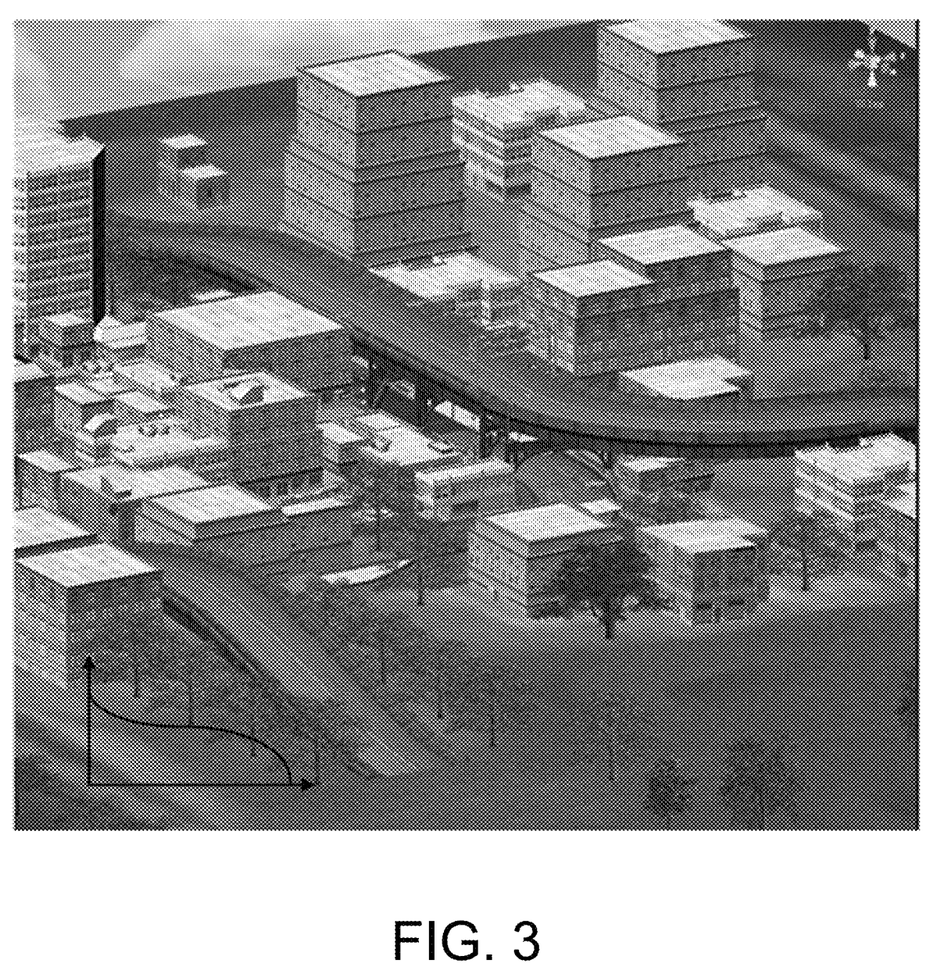
FIG. 3 is a schematic diagram of a virtual scene of an embodiment.
Figure 4:
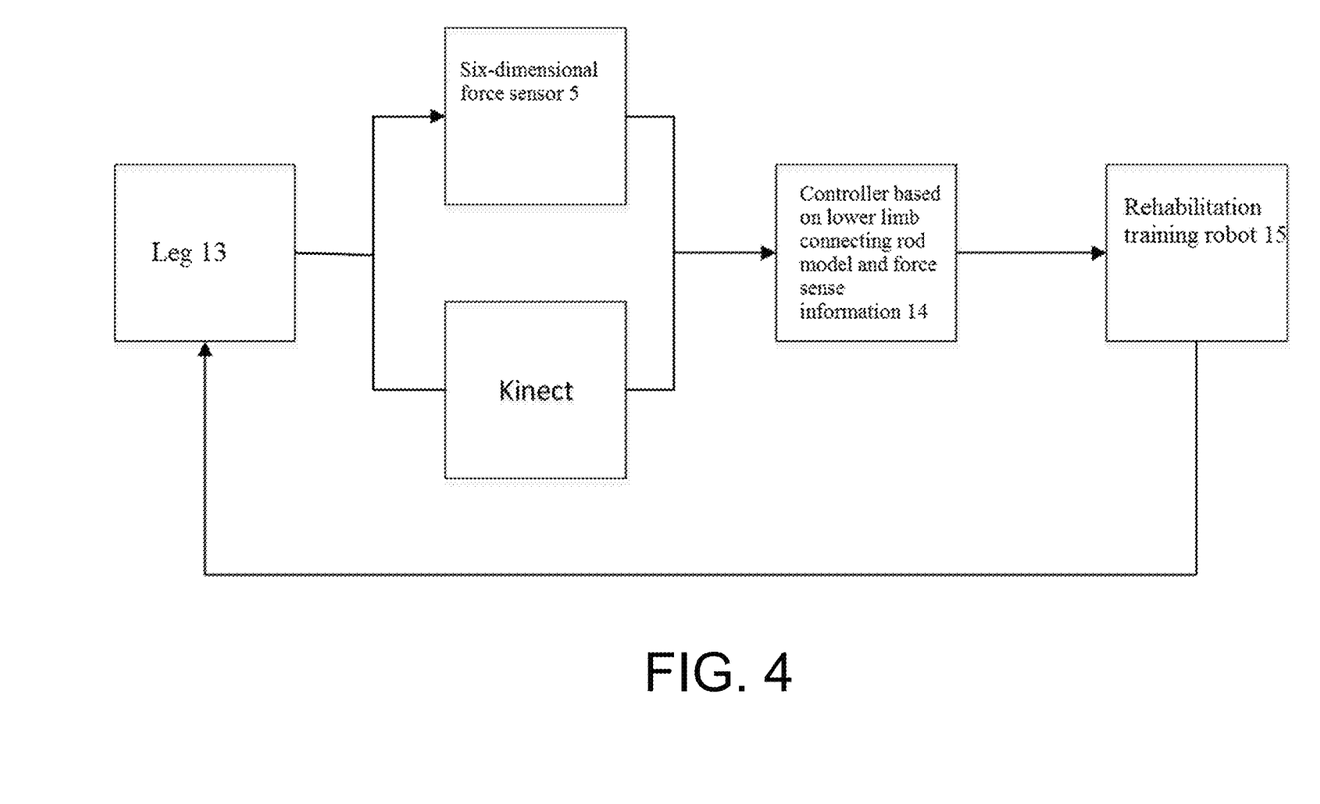
FIG. 4 is a system block diagram of an embodiment.

The above progressive rehabilitation training control method is as follows.

a) First, the human body leg gravity compensation model is imported, and run along a preset trajectory (as shown in the figure) for several cycles in a working space, and $_E^S E$ and $C_f$ in the model are corrected by an acquired force sensor value and a corresponding posture to obtain a model for the user finally.

b) The leg posture of the user is detected by Kinect, a plantar force of the user is detected by the force sensor, and the robot is controlled to interact with the user according to a virtual reality scene in step c).

c) In combination with a gentle slope virtual scene, an active force required by the user at this moment is determined according to the gradient of a gentle slope where a virtual character is located currently, and the robot is controlled according to regulations of step d) through the acquired force and posture situations in step b).

d) A gravity value of a current posture is obtained according to the human body leg gravity compensation model, a value of an active force required currently is obtained according to a virtual reality model, the sizes of values obtained by the force sensor currently are compared, if a value obtained by the six-dimensional force sensor currently is greater than the sum of the gravity value and the required active force, the motion is allowed, otherwise the robot is stationary.

Embodiment

Figure 5:
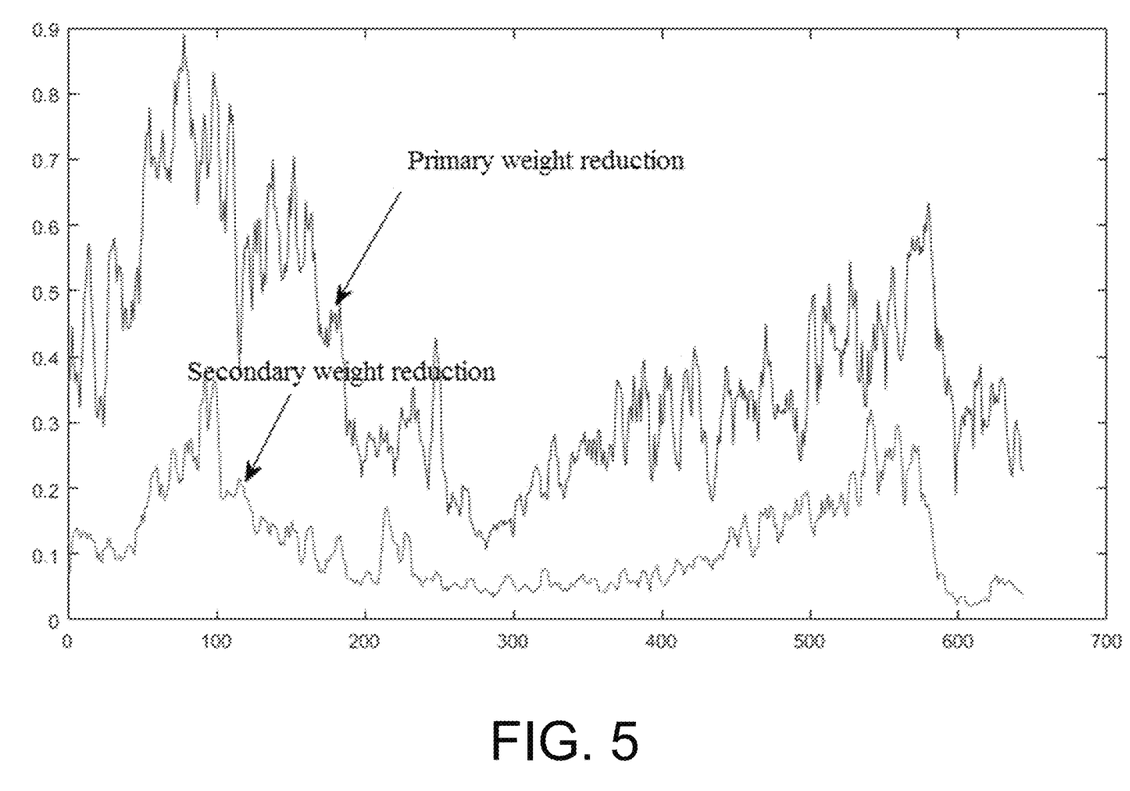
FIG. 5 is a graph of surface EMG signals in primary and secondary weight reduction modes of an embodiment.

A patient with lower limb dyskinesia is chosen for rehabilitation training. The patient has some exercise ability in the lower limbs, but the muscle strength is not enough to complete the exercise in a larger space. The patient uses a single-degree-of-freedom lower limb rehabilitation training robot for leg rehabilitation training. A preset motion space is achieved through robot assistance, after establishing the model according to the above, primary and secondary weight reduction modes are set, and surface EMG signals of the lower limbs of the patient during the training process are recorded, as shown in FIG. 5. It can be seen that in the secondary weight reduction mode, the surface EMG signal of the patient is significantly weaker than that in the primary weight reduction mode, indicating that the patient's autonomy is less, that is, the weight reduction effect is better. During the rehabilitation training process, the gradient of a virtual scene is gradually increased in a rehabilitation cycle, that is, the value of a required active force is increased, and the physical function of the patient is progressively restored until the limb motion may be freely controlled.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A control method of the virtual scene interactive rehabilitation training robot based on a lower limb connecting rod model and force sense information, wherein the virtual sense interactive rehabilitation training robot comprises a thigh mechanical arm, a calf mechanical arm and a foot mechanical arm that are movably connected in sequence from top to bottom, wherein a six-dimensional force sensor is installed on the foot mechanical arm, the corresponding thigh mechanical arm, calf mechanical arm and foot mechanical arm in sequence are configured to be fixed to a thigh, a calf and a foot of a patient, and a three-connecting rod series-connected mechanical arm assembly is configured to connect the thigh, the calf and the foot of a leg of the patient, and the control method comprising:

connecting the thigh, the calf and the foot of the leg of the patient to the three-connecting rod series-connected mechanical arm assembly;

constructing a human body leg gravity compensation model;

detecting a leg posture of the patient by a motion sensing input device; and detecting an interaction force between a limb of the patient and a rehabilitation robot by the six-dimensional force sensor, wherein when the leg of the patient is relaxed in a state of no active force, driving, by the rehabilitation training robot, the limb of the patient to move slowly at a constant speed for several cycles along a preset trajectory in a controller, correcting the human body leg gravity compensation model after acquiring posture information of the patient and corresponding force information, adopting a progressive rehabilitation training method for the human body leg gravity compensation model after correcting the model, and controlling, according to a set weight reduction ratio, the motion of the rehabilitation robot by judging data of a plantar six-dimensional force sensor.

2. The control method of the virtual scene interactive rehabilitation training robot based on a lower limb connecting rod model and force sense information according to claim 1, wherein the human body leg gravity compensation model is as follows:

(1) a leg of a human body is connected to the three-connecting rod series-connected mechanical arm assembly having three series-connected connecting rods, the foot, the calf and the thigh are a connecting rod T0S0, a connecting rod S0F0 and a connecting rod F0S0, respectively, the foot and the six-dimensional force sensor are relatively stationary, and parts other than the leg of the human body are equated connected to a base (Base) in a stationary state;

(2) a hip joint coordinate system, a knee joint coordinate system and an ankle joint coordinate system are established, the six-dimensional force sensor on the robot and the foot of the human body of the patient are relatively stationary, then a coordinate system is established by taking a contact point between the six-dimensional force sensor and the foot of the patient as an S0 origin, an X axis, a Y axis and a Z axis of the coordinate system are parallel to an X axis, a Y axis and a Z axis of the ankle joint coordinate system, respectively, and positive directions of the three axes of the coordinate system are the same as a positive direction of the ankle joint coordinate system;

in a center of a mass coordinate system corresponding to the thigh, the calf and the foot of the patient, centers of mass ETO, ECO and EFO of corresponding parts of the leg are taken as origins, a vertical downward direction is a Z axis positive direction, an outward direction perpendicular to a human body plane is an X axis positive direction, and a direction perpendicular to an XZ plane toward the human body is a Y axis positive direction;

(3) it is assumed that $^{ET}F_{mg}$, $^{EC}F_{mg}$ and $^{EF}F_{mg}$ are gravity vectors of the thigh, the calf and the foot in a geodetic coordinate system, $_B^A R$ is a rotation matrix from a B coordinate system to an A coordinate system, $_B^A T_f$ is a force parameter conversion matrix from the B coordinate system to the A coordinate system, and $^A P_{BORG}$ is a representation of an origin of the B coordinate system in the A coordinate system; an equation is obtained:

$$_B^A T_f = \begin{bmatrix} _B^A R & 0 \\ ^A P_{BORG} \times _B^A R & _B^A R \end{bmatrix}$$

an interference force caused by a thigh gravity and its joint damping with a trunk and due to individual errors of average characteristic parameters is represented as $^{ST}F_{mg}$ in a six-dimensional force sensor coordinate system; an interference force caused by a calf gravity and its joint damping with the thigh and due to the individual errors of the average characteristic parameters is represented as $^{SC}F_{mg}$ in the sensor coordinate system; an interference force caused by a foot gravity and its joint damping with the calf and due to the individual errors of the average characteristic parameters is represented as $^{SF}F_{mg}$ in the sensor coordinate system; $_{ET}^{S}E$, $_{EC}^{S}E$ and $_{EF}^{S}E$ are interference correction parameter matrices caused due to the individual errors of the average characteristic parameters of the thigh, the calf and the foot, respectively; $_{ET}^{S}T_f$, $_{EC}^{S}T_f$ and $_{EF}^{S}T_f$ are parameter conversion matrices of the thigh, the calf and the foot from the geodetic coordinate system to the force sensor coordinate system, respectively;

$C_f$ is an interference correction parameter matrix caused due to joint damping, left superscripts B, T and C representing the hip, knee, and ankle joints, respectively; and $^{S}F_{mg}$ is a plantar force acting on a force sensor;

following equations are derived:

$$^{ST}F_{mg} = {_{ET}^{S}E} \times {_{ET}^{S}T_f} \times {^{ET}F_{mg}} + {_{ET}^{S}T_f} \times {_{T}^{ET}R} \times {_{B}^{T}R} \times {^{B}C_f}$$

$$^{SC}F_{mg} = {_{EC}^{S}E} \times {_{EC}^{S}T_f} \times {^{EC}F_{mg}} + {_{EC}^{S}T_f} \times {_{C}^{EC}R} \times {_{T}^{C}R} \times {^{T}C_f}$$

$$^{SF}F_{mg} = {_{EF}^{S}E} \times {_{EF}^{S}T_f} \times {^{EF}F_{mg}} + {_{EF}^{S}T_f} \times {_{F}^{EF}R} \times {_{C}^{F}R} \times {^{C}C_f}$$

$$^{S}F_{mg} = {^{ST}F_{mg}} + {^{SC}F_{mg}} + {^{SF}F_{mg}}$$

(4) the human body leg gravity compensation model is obtained by steps (1) to (2), an initial model is established by inputting height and weight parameters of the patient into the controller, plantar six-dimensional force sensor parameters in the absence of an active force in any posture of a user are acquired by the model, actual parameters and the parameters acquired by the model are input into the controller, and the rehabilitation robot is controlled to interact with the patient using a progressive rehabilitation training control method.

3. The control method of the virtual scene interactive rehabilitation training robot based on a lower limb connecting rod model and force sense information according to claim 2, wherein the method of establishing the three coordinate systems in step (2) is:

the hip joint coordinate system: a human body stands with legs closed, a center point T0 at a connection between the thigh and the trunk is taken as an origin of the hip joint coordinate system, an axial downward direction along the thigh is a TX axis positive direction, an outward direction perpendicular to a front surface of the human body is a TZ axis positive direction, and a direction perpendicular to a TXTZ plane toward the trunk of the human body is a TY axis positive direction;

the knee joint coordinate system: a human body stands with legs closed, a center point C0 at a connection between the thigh and the calf is taken as an origin of the knee joint coordinate system, an axial downward direction along the knee is a CX axis positive direction, an outward direction perpendicular to a front surface of the human body is a CZ axis positive direction, and a direction perpendicular to a CXCZ plane toward the trunk of the human body is a CY axis positive direction;

the ankle joint coordinate system: a human body stands with legs closed, a center point F0 at a connection between the thigh, the calf and the foot is taken as an origin of the ankle joint coordinate system, an axial outward direction along the foot is an FX axis positive direction, a direction perpendicular to an F0FX plane and an F0C0 plane toward the trunk of the human body is an FY axis positive direction, and a direction perpendicular to an FXFY plane toward the trunk of the human body is an FZ axis positive direction; and in a coordinate system established by taking a contact point between the six-dimensional force sensor and the foot of the patient as an S0 origin, an SX axis is parallel to an FX axis, an SY axis is parallel to an FY axis, and an SZ axis is parallel to an FZ axis.

4. The control method of the virtual scene interactive rehabilitation training robot based on a lower limb connecting rod model and force sense information according to claim 2, wherein the specific process of the progressive rehabilitation training control method is as follows:

(A) first, importing the human body leg gravity compensation model into the controller, running along a preset trajectory for several cycles in a working space, and correcting $_{E}^{S}E$ and $C_f$ in the model by an acquired six-dimensional force sensor value and a corresponding posture to obtain a characteristic model for the patient finally;

(B) detecting the leg posture of a user using the motion sensing input device, detecting a plantar force of the user using the six-dimensional force sensor, and controlling the robot to interact with the patient according to a virtual reality scene in step (C);

(C) in combination with a gentle slope virtual scene, according to a gradient of a gentle slope where a virtual character is located currently, determining an active force required by the patient at this moment through the human body leg gravity compensation model, and controlling the robot to move according to regulations of step (D) through the acquired force and posture situations in step (D); and (D) obtaining a gravity value of a current posture according to the human body leg gravity compensation model, obtaining a value of an active force required currently according to a virtual reality model, comparing the sizes of values obtained by the force sensor currently, if a value obtained by the six-dimensional force sensor currently is greater than a sum of the gravity value and the active force required, allowing the robot to move, or otherwise keeping the robot stationary.

* * * * *